(12) United States Patent
Fujii et al.

(10) Patent No.: US 7,708,990 B2
(45) Date of Patent: May 4, 2010

(54) COENZYME Q COMPOSITIONS PERSISTING IN BLOOD

(75) Inventors: Kenji Fujii, Kobe (JP); Taizo Kawabe, Takasago (JP); Hiroshi Kubo, Kobe (JP)

(73) Assignee: Kaneka Corporation, Osaka (JP)

( * ) Notice: Subject to any disclaimer, the term of this patent is extended or adjusted under 35 U.S.C. 154(b) by 1059 days.

(21) Appl. No.: 11/085,181

(22) Filed: Mar. 22, 2005

(65) Prior Publication Data

US 2006/0073131 A1    Apr. 6, 2006

Related U.S. Application Data

(60) Provisional application No. 60/559,967, filed on Apr. 7, 2004.

(30) Foreign Application Priority Data

Mar. 23, 2004 (JP) .............................. 2004-084247

(51) Int. Cl.
  A61K 38/43    (2006.01)
  A01N 31/14    (2006.01)
(52) U.S. Cl. ...................... 424/94.1; 514/718; 514/720; 514/824; 514/878; 514/879
(58) Field of Classification Search ................ 424/94.1; 514/718, 720, 824, 878, 879
See application file for complete search history.

(56) References Cited

U.S. PATENT DOCUMENTS 4,068,003 A    1/1978  Miyata
6,184,255 B1   2/2001  Mae et al.
2004/0248991 A1  12/2004  Fujii et al.
2005/0008630 A1   1/2005  Ueda et al.

(Continued)

FOREIGN PATENT DOCUMENTS

EP    1 475 363 A1    11/2004

(Continued)

OTHER PUBLICATIONS

Zaghloul et al, Bioavailability Assessment of Oral Coenzyme Q10 Formulations in Dogs, Drug Development and Industrial Pharmacy, 2002, pp. 1195-1200, vol. 28-No. 10.

(Continued)

*Primary Examiner*—Ardin Marschel
*Assistant Examiner*—Zohreh Vakili
(74) *Attorney, Agent, or Firm*—Sughrue Mion, PLLC

(57) ABSTRACT

The object of the present invention is to provide a composition maintaining a blood coenzyme Q concentration at a high level in blood for a prolonged period of time, in order to surely attain an effect of coenzyme Q, which can be expected to manifest a superior effect in maintaining health in humans and animals.

By using a composition which comprises a coenzyme Q being a mixture of a reduced coenzyme Q and an oxidized coenzyme Q with the proportion of the reduced coenzyme Q to the whole coenzyme Q of more than 95% by weight, the present invention can attain a high maximum blood concentration of a coenzyme Q as well as long maintenance of high concentration of coenzyme Q in blood for a prolonged period of time, and the area under the blood concentration curve (AUC) can be expanded.

16 Claims, 1 Drawing Sheet

U.S. PATENT DOCUMENTS

2006/0165672 A1 * 7/2006 Fujii et al. .................. 424/94.1

FOREIGN PATENT DOCUMENTS

| GB | 2 178 662 A | 2/1987 |
| JP | 52-99220 | 8/1977 |
| JP | 52-99222 | 8/1977 |
| JP | 62-59208 | 3/1987 |
| JP | 7-330584 | 12/1995 |
| JP | 7-330593 | 12/1995 |
| JP | 10-45594 | 2/1998 |
| JP | 10-109933 | 4/1998 |
| JP | 10-287560 | 10/1998 |
| JP | 2002-265985 A | 9/2002 |
| JP | 2003-119127 A | 4/2003 |
| WO | WO 98/07417 | 2/1998 |
| WO | WO 01/52822 A1 | 7/2001 |
| WO | WO 01/64041 A1 | 9/2001 |
| WO | WO 03/032967 A1 | 4/2003 |
| WO | WO 03/032968 A1 | 4/2003 |
| WO | WO 03/062182 A1 | 7/2003 |
| WO | WO 2004/066988 A1 | 8/2004 |

OTHER PUBLICATIONS

Miles et al, Bioequivalence of Coenzyme Q10 From Over-The-Counter Supplements, Nutrition Research, 2002, pp. 919-929, vol. 22.

* cited by examiner

COENZYME Q COMPOSITIONS PERSISTING IN BLOOD

This application claims priority from U.S. Provisional Application No. 60/559,967 filed on Apr. 7, 2004 in the United States Patent and Trademark Office, the disclosure of which is incorporated by reference herein in its entirety.

TECHNICAL FIELD

The present invention relates to a composition comprising, as the active ingredients, a reduced coenzyme Q represented by the following formula (1) and an oxidized coenzyme Q represented by the following formula (2) which composition enables the coenzyme Q concentration in blood to be maintained at a high concentration level for a prolonged period of time (n in the formulas representing an integer of 1 to 12).

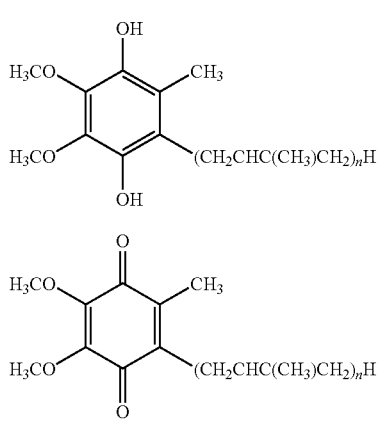

BACKGROUND ART

A coenzyme Q is an essential component widely distributed in living bodies from bacteria to mammals. In humans, it is known that the main component thereof is coenzyme $Q_{10}$ whose coenzyme Q side chain has 10 repeating structures. Coenzyme $Q_{10}$ is a physiological component occurring as an electron transfer system constituent in mitochondria in cells of living bodies and performs its function as a transmitter component in the electron transfer system by repeatedly undergoing oxidation and reduction in living bodies. The coenzyme Q is known to show energy producing, membrane stabilizing and antioxidant activities in living bodies and is in wide use. Among coenzyme $Q_{10}$ species, oxidized $Q_{10}$ (ubiquinone or ubidecarenone) is used as a drug for congestive heart failure and thus is known to effectively act on the heart. As for its effects, improvement in oxygen utilization efficiency in heart muscle, activation of ATP production in heart muscle, and improvement in heart function, and the like, have been reported. In the fields other than the pharmaceutical field, effects as a nutrient or nutrient supplement, like those of vitamins, have been reported. A tissue metabolism activating composition comprising a mixture of ubiquinone and a dried yeast powder (Japanese Kokai Publication Sho62-59208), improvements in symptoms of myasthenia gravis by a composition comprising ubiquinone (Japanese Kokai Publication Sho52-99220) and an erythrocyte increasing effect of a composition comprising ubiquinone (Japanese Kokai Publication Sho52-99222, and the like, have also been reported. Furthermore, a fatigue relieving effect has been reported (Japanese Kokai Publication Hei07-330584; Japanese Kokai Publication Hei07-330593; Japanese Kokai Publication Hei10-287560).

As regards reduced coenzyme $Q_{10}$, unlike the oxidized form, there is no report about the utility thereof. This is because reduced coenzyme $Q_{10}$ is readily susceptible to air oxidation and, therefore, cannot have been evaluated for utility. One of the reasons why reduced coenzyme $Q_{10}$ has not been evaluated for utility is that it is generally known that even oxidized coenzyme $Q_{10}$ is administered, it undergoes reduction in living bodies and this results in an increase in reduced coenzyme $Q_{10}$ level and it has been considered that oxidized coenzyme $Q_{10}$ and reduced coenzyme $Q_{10}$ should be equal in efficacy to living bodies. Previously, we disclosed that the oral absorbability of a coenzyme Q is increased by the coexistence of a reduced coenzyme Q as compared with the corresponding oxidized coenzyme Q alone (Japanese Kokai Publication Hei10-109933) and showed that the utilization of a reduced coenzyme Q is effective in increasing the oral absorbability. This composition gave a maximum plasma concentration ($C_{max}$) about twice higher as compared with the oxidized coenzyme Q alone. However, the rate of disappearance thereof is rapid and no improvement in maintenance of high concentration of coenzyme Q in blood was observed.

It is well known from the experience in drug development research works, and the like, that, in the case of such a hydrophobic substance as coenzymes Q, not only an increase in $C_{max}$ but also an improvement in maintenance of high concentration of coenzyme Q in blood (AUC) is generally desirable for effective manifestation of an effect thereof in living bodies, whatever the effect is. Thus, although an increase in $C_{max}$ is indeed an important factor for effectively using substances not so strong in effects, such as coenzymes Q, various effects can be expected when a high blood level can be maintained. For example, if a coenzyme Q maintains its high concentration in blood for a prolonged period of time, its antioxidant activity will be maintained at a high level and it can be expected for the frequency of occurrence of arteriosclerosis, diabetic complications, cerebral diseases, renal diseases and like diseases caused by oxidative stresses in blood to be efficiently decreased. Further, while coenzyme $Q_{10}$ is thought to migrate to various tissues or organs and activate the energy production or enhance the antioxidant activity in respective organs to produce various biological effects, the maintenance of high concentration of coenzyme $Q_{10}$ in blood for a prolonged period of time can be expected to increase the probability of its migration to various tissues or organs, since its migration to respective tissues or organs takes place through blood. Therefore, for increasing the probability of manifestation of a number of effects of coenzyme $Q_{10}$, it is necessary to maintain its blood concentration at high levels.

SUMMARY OF THE INVENTION

For further increasing the usefulness of coenzymes Q, the present invention provides a coenzyme Q composition for maintaining high concentration of coenzyme Q in blood which can attain a high maximum blood concentration after administration as well as long maintenance of high concentration of coenzyme Q in blood, and a method of maintaining the blood concentration of a coenzyme Q at high levels.

The present inventors made intensive investigations concerning reduced coenzyme Q-containing compositions and, as a result, found that when the proportion of a reduced coenzyme Q to the whole coenzyme Q is higher than 95% by weight, longer maintenance of its high concentration in blood can be realized as compared with the conventional compositions. Based on such finding, they have now completed the present invention.

DETAILED DESCRIPTION OF THE INVENTION

Figure 1:
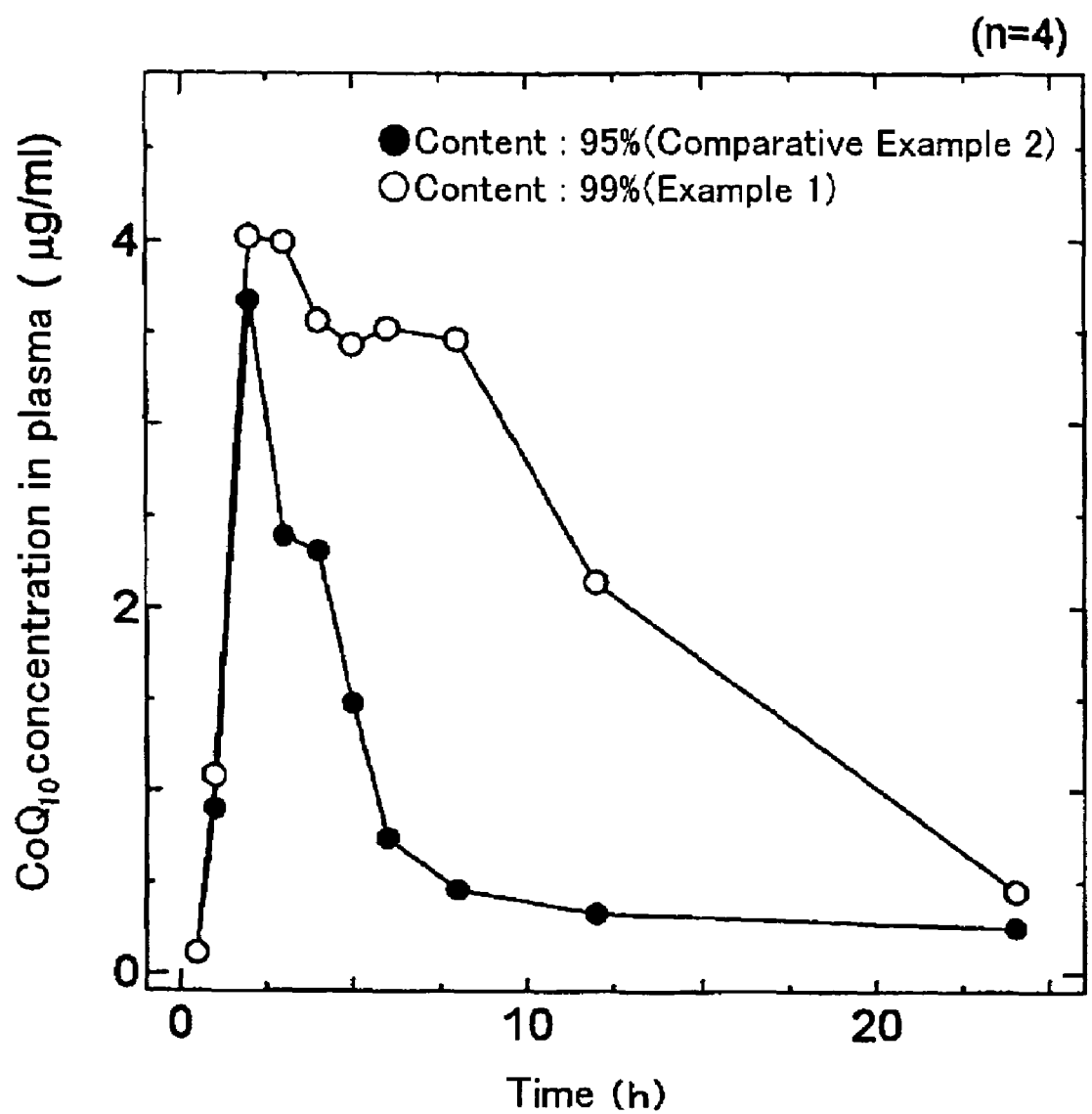
FIG. 1 shows the time courses of the rat plasma coenzyme $Q_{10}$ levels ($CoQ_{10}$) in Example 1 and Comparative Example 2. The ordinate denotes the $CoQ_{10}$ concentration in plasma, and the abscissa denotes the time (h) after administration of reduced coenzyme $Q_{10}$ to rats. The marks ● indicate the data obtained in Comparative Example 2 (reduced coenzyme $Q_{10}$ content: 95% by weight), and the marks ○ indicate the data obtained in Example 1 (reduced coenzyme $Q_{10}$ content: 99% by weight)

Thus, the present invention relates to a coenzyme Q composition for maintaining high concentration of coenzyme Q in blood which comprises, as the active ingredients, a reduced coenzyme Q represented by the following formula (1), wherein n represents an integer of 1 to 12, and an oxidized coenzyme Q represented by the following formula (2), wherein n represents an integer of 1 to 12, with the proportion of the reduced coenzyme Q to the whole coenzyme Q of more than 95% by weight.

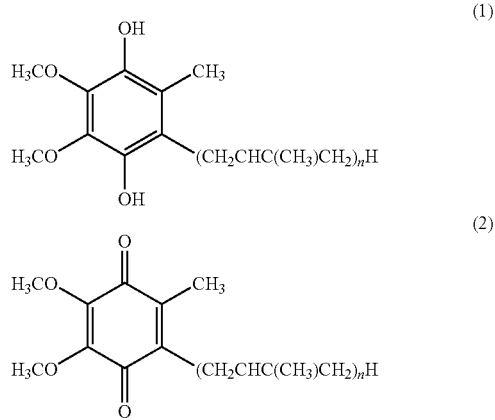

The present invention also relates to a method of maintaining the blood concentration of a coenzyme Q at high levels for a prolonged period of time which comprises administering a composition comprising a reduced coenzyme Q represented by the above formula (1) and an oxidized coenzyme Q represented by the above formula (2), with the proportion of the reduced coenzyme Q to the whole coenzyme Q of more than 95% by weight.

The coenzyme Q composition for maintaining high concentration of coenzyme Q in blood according to the invention is a composition making it possible to maintain the blood concentration of a coenzyme Q (sum of the blood concentrations of the reduced coenzyme Q and oxidized coenzyme Q) at high levels for a long period of time. It is known that about 40 to 90% of a coenzyme Q generally occurs as the reduced form in living bodies. The method of obtaining the reduced coenzyme Q is not particularly restricted but, for example, the method comprising obtaining the coenzyme Q by any of the conventional methods, such as synthesis, fermentation or extraction from a natural product, subjecting the preparation to chromatography and concentrating the eluate reduced coenzyme Q fraction may be employed. In this case, it is also possible to add an ordinary reducing agent, such as sodium borohydride or sodium dithionite (sodium hydrosulfite) to the coenzyme Q obtained by the above-mentioned extraction, for instance, according to need, reduce the oxidized coenzyme Q contained in the above-mentioned coenzyme Q to the reduced coenzyme Q in the conventional manner and then concentrate the thus-obtained product by chromatography. It is also possible to obtain it by reacting an already existing high-purity coenzyme Q with such a reducing agent as mentioned above. It is further possible to use reduced coenzyme Q-containing microbial cells or the like. It is important that the thus-obtained reduced coenzyme Q has an oxidized coenzyme Q content of lower than 5% by weight.

Generally, the proportion of the reduced form in a coenzyme Q can be determined by the method comprising quantitating the oxidized coenzyme Q and reduced coenzyme Q in a sample by means of a high-performance liquid chromatography (HPLC) system using a UV detector, followed by calculation based on the quantity ratio determined, or the method comprising calculating the ratio between the oxidized coenzyme Q and reduced coenzyme Q based on the peak areas obtained by using a HPLC system with an electrochemical detector incorporated therein. The system with an electrochemical detector incorporated therein can determine an oxidizing or reducing substance specifically and is high in sensitivity and, therefore, is extremely useful in determining the proportion of the reduced form occurring in trace amounts in living bodies or samples. All the proportions of the reduced coenzyme Q as reported herein are the values obtained by using an HPLC system with an electrochemical detector incorporated therein.

As mentioned above, we found that when a composition containing both a reduced coenzyme Q and an oxidized coenzyme Q was orally administered, a higher plasma level of the coenzyme Q could be attained as compared with the single administration of the oxidized coenzyme Q. However, although this composition could increase the $C_{max}$ to a level about twice that obtained upon single administration of oxidized coenzyme $Q_{10}$ alone, the area under the blood concentration curve (AUC), which is an indicator of the maintenance of high concentration of coenzyme Q in blood, was about 1.3 times and thus the effect on the maintenance of high concentration of coenzyme Q in blood as observed was not so significant. We considered that, for allowing a coenzyme Q to fully produce its physiological effects, it was important to bring about an improvement not only in maximum blood concentration but also in maintenance of high concentration of coenzyme Q in blood, and made investigations in an attempt to develop a composition which would satisfy both the requirements. Meanwhile, it is thought that coenzymes Q are absorbed into the body from the intestinal tract via the lymphatic vessel. It appears necessary to develop a composition suited for lymphatic absorption to thereby maintain the feeding from lymph to blood for a prolonged period of time and thus attain the maintenance of high concentration of coenzyme Q in blood. This time, as a result of investigations, we found that high blood concentrations and long maintenance of high concentration of coenzyme Q in blood can be attained when a composition in which the proportion of a reduced coenzyme Q is higher than 95% by weight of the whole coenzyme Q is used. In Japanese Kokai Publication Hei10-109933, there is an example reported in which the proportion of reduced coenzyme $Q_{10}$ is not higher than 95%. At that time, it was difficult to maintain a composition having a reduced coenzyme $Q_{10}$ proportion of more than 95% by those methods of production and methods of preserving which were available then. However, as a result of later investigations made by us, a technology of maintaining a composition in which the proportion in question exceeds 95% has been established (Japanese Kokai Publication 2003-113129). By using this high purity composition in the present study, we found that the maintenance of high concentration of coenzyme Q in blood can be remarkably improved as compared with the conventional compositions with a reduced coenzyme $Q_{10}$ proportion of not higher than 95%.

The coenzyme Q composition for maintaining high concentration of coenzyme Q in blood according to the invention is a composition containing a reduced coenzyme Q and an oxidized coenzyme Q, in which the proportion of the reduced coenzyme Q to the total amount of the coenzyme Q exceeds 95% by weight, more preferably not lower than 97% by weight. The upper limit to the proportion of the reduced coenzyme Q in the coenzyme Q is not particularly restricted provided that it is lower than 100% by weight. Preferably, it is not higher than 99.999% by weight and, more preferably, it is not higher than 99.9% by weight.

The reduced coenzyme Q which can be used in the practice of the present invention includes those in which the number (n in the formula) of repetitions of the side chain unit is 1 to 12, as shown by the above formula (1) and, among them, the one in which the number of repetitions of the side chain unit is 10, namely reduced coenzyme $Q_{10}$, can be used most appropriately.

The oxidized coenzyme Q which can be used in the practice of the present invention includes those in which the number (n in the formula) of repetitions of the side chain unit is 1 to 12, as shown by the above formula (2) and, among them, the one in which the number of repetitions of the side chain unit is 10, namely oxidized coenzyme $Q_{10}$, can be used most appropriately.

The content of the coenzyme Q (sum of the reduced coenzyme Q and oxidized coenzyme Q) in the coenzyme Q composition for maintaining high concentration of coenzyme Q in blood according to the invention is preferably 0.01 to 70% by weight, more preferably 1 to 50% by weight.

The coenzyme Q composition for maintaining high concentration of coenzyme Q in blood according to the invention may further comprise an antioxidant substance and/or an antioxidant enzyme. The antioxidant substance is not particularly restricted but includes such suitable examples as vitamin E, vitamin E derivatives, vitamin C, vitamin C derivatives, probucol, lycopene, vitamin A, carotenoids, vitamin B, vitamin B derivatives, flavonoids, polyphenols, glutathione, pyrroloquinoline quinone, Pycnogenol, Flavangenol, selenium, lipoicacid, lipoicacid derivatives and the like. These antioxidant substances may be used singly or two or more of them may be used in admixture.

The antioxidant enzyme is not particularly restricted but includes such suitable examples as superoxide dismutase (SOD), glutathione peroxidase, glutathione S-transferase, glutathione reductase, catalase, and ascorbic acid peroxidase, and the like. Such antioxidant enzymes may be used singly or two or more of them may be used in admixture.

The coenzyme Q composition for maintaining high concentration of coenzyme Q in blood according to the invention may further contain at least one other nutrient/tonic component. The nutrient/tonic component is not particularly restricted but includes, as suitable examples, creatine, carnitine, taurine, vitamin $B_1$, vitamin B derivatives, and amino acids, and the like. Such nutrient/tonic components maybe used singly or two or more of them may be used in admixture.

The coenzyme Q composition for maintaining high concentration of coenzyme Q in blood according to the invention can additionally contain a nutrient supplement component. The nutrient supplement component is not particularly restricted but includes amino acids, metal ions, saccharides, proteins, fatty acids, vitamins and the like. Such nutrient supplement compositions may be used singly or two or more of them may be used in admixture.

According to the present invention, the blood concentration of a coenzyme Q can be maintained at high levels for a prolonged period of time by administering a composition comprising the corresponding reduced coenzyme Q and oxidized coenzyme Q, with the proportion of the reduced coenzyme Q to the whole coenzyme Q of more than 95% by weight.

When the coenzyme Q composition for maintaining high concentration of coenzyme Q in blood according to the invention is administered at a dose of 100 mg/kg body weight in terms of weight of coenzyme Q, to rats for example, a blood coenzyme Q concentration of at least 1.0 ug/ml can be maintained for 4 to 8 hours, preferably 4 to 12 hours. Furthermore, when the composition comprising a reduced coenzyme Q and an oxidized coenzyme Q according to the invention is administered, the half-life of the coenzyme Q in blood can be prolonged to 7 hours or longer, preferably 8 hours or longer, more preferably 10 hours or longer.

When the method according to the invention is employed, the coenzyme Q concentration in blood can be maintained at a level at least half the maximum blood concentration attained after administration of the composition preferably over 8 hours or longer, more preferably 10 hours or longer.

The dose of the coenzyme Q composition for maintaining high concentration of coenzyme Q in blood according to the invention which is to be employed for maintaining the blood coenzyme Q concentration for a prolonged period of time is not particularly restricted but is preferably 30 mg/day to 200 mg/day in terms of weight of coenzyme Q for one adult person.

In this manner, the effects or virtues of the reduced coenzyme Q can be effectively manifested. The effects or virtues of the reduced coenzyme Q include, but are not limited to, for example, the prevention and alleviation of aging, fatigue, diabetes and diabetic complications, arteriosclerosis, hyperlipidemia, hypertension, hypotension, climacteric disturbances, vertigo, nephritis, infectious diseases, Alzheimer's disease, Parkison's disease, Huntington's chorea, mitochondrial abnormality, Crohn's disease, ulcerative colitis, cancer, myasthenia gravis, obesity, skin diseases, wrinkles, sunburn, skin eruptions, peribdontal diseases, stresses, allergies, blind headache, defect of memory, agenosis and the like, and further life prolongation.

The mode of administration is not particularly restricted but may be oral administration or administration in the form of parenteral solutions, drip infusion preparations, suppositories, transmucosal preparations, and inhalations. Oral administration by an oral formulation is preferred, however.

The dosage form of the coenzyme Q composition for maintaining high concentration of coenzyme Q in blood according to the invention as an oral formulation is not particularly restricted but may include, for example, powders, granules obtained by adding a binder to a powder, and capsule preparations obtained by filling capsules with a powder or granules. It is also possible to prepare soft capsule preparations by adding a natural oil, an oily higher fatty acid, a higher fatty acid monoglyceride or a surfactant or a mixture of these, for instance, to a coenzyme Q composition and filling soft capsules with the resulting oily substance as it is or as a slurry. In this case, gelatin-based capsules or other water-soluble polymeric substance-based ones can be used, for example. Microcapsules are also included among such capsules. Alternatively, the coenzyme Q composition may be rendered liquid to give health drink preparations. The most suitable dosage form includes, but is not limited to, soft capsules with an oily form of the coenzyme Q composition, together with a fat and oil and/or a surfactant, as such or as slurry filled therein.

Preferred are capsules, tablets, powders and solutions.

In the coenzyme Q composition for maintaining high concentration of coenzyme Q in blood according to the invention, there may further additionally incorporated an appropriate amount of at least one pharmaceutically acceptable preparation ingredient material, in addition to the above-mentioned reduced coenzyme Q and oxidized coenzyme Q, in the conventional manner. Such material is not particularly restricted but may be, for example, an excipient, disintegrant, lubricants, binder, antioxidant, colorant, aggregation inhibitor, absorption enhancer, solubilizing agent, stabilizer or the like.

The excipient is not particularly restricted but includes, for example, white sugar, lactose, glucose, corn starch, mannitol, crystalline cellulose, calcium phosphate, calcium sulfate and the like.

The disintegrant is not particularly restricted but includes, for example, starch, agar, calcium citrate, calcium carbonate, sodium hydrogen carbonate, dextrin, crystalline cellulose, carboxymethylcellulose, tragacanth and the like.

The lubricant is not particularly restricted but includes, for example, talc, magnesium stearate, polyethylene glycol, silica, hardened vegetable oils and the like.

The binder is not particularly restricted but includes, for example, ethylcellulose, methylcellulose, hydroxypropylmethylcellulose, tragacanth, shellac, gelatin, gum arabic, polyvinylpyrrolidone, polyvinyl alcohol, polyacrylic acid, polymethacrylic acid, sorbitol and the like.

The antioxidant is not particularly restricted but includes, for example, ascorbic acid, tocopherol, vitamin A, β-carotene, sodium hydrogen sulfite, sodium thiosulfate, sodium pyrosulfite, citric acid, derivatives of these, and the like.

The colorant is not particularly restricted but includes, for example, those approved for addition to pharmaceuticals, and the like.

The aggregation inhibitor is not particularly restricted but includes, for example, stearic acid, talc, light anhydrous silicic acid, hydrous silicon dioxide and the like.

The absorption enhancer is not particularly restricted but includes, for example, higher alcohols, higher fatty acids, glycerol fatty acid esters and like surfactants, and the like.

The solubilizing agent is not particularly restricted but includes, for example, fumaric acid, succinic acid, malic acid and like organic acids, and the like.

The stabilizer is not particularly restricted but includes, for example, benzoic acid, sodium benzoate, ethyl parahydroxybenzoate and the like.

In cases where the coenzyme Q composition for maintaining high concentration of coenzyme Q in blood according to the invention takes an ordinary food form, the food form is not particularly restricted but includes, for example, edible fat and oil compositions, cooking oils, spray oils, butters, margarines, shortenings, whipped creams, condensed milks, whiteners, dressings, pickling solutions, breads, cakes, pies, cookies, Japanese sweets, snack foods, fried cookies/sweets, chocolates, chocolate candies, rice crackers, roux, sauces, drippings, toppings, ice cream/iced sherbet, noodles, bakery mixes, fried foods, processed meat products, fish paste-based products, frozen entrees, frozen stock farm products, frozen agricultural products, other frozen foods, boiled rice products, jams, cheeses, cheese foods, cheese-like foods, gums, candies, fermented milk products, canned foods, drinks and beverages, and the like. The processes for preparing these foodstuffs are desirably carried out at lowered temperatures and/or under deoxygenated conditions so that the reduced coenzyme Q may be prevented from being oxidized.

The composition of the invention is suited for effective taking of coenzymes Q. That a high blood concentration is maintained is important in efficient manifestation of various effects of coenzymes Q, and the composition of the invention can be expected to more efficiently produce the effects of coenzymes Q. Further, it is possible to maintain the blood coenzyme Q concentration at high levels for a prolonged period of time by the method described herein.

BEST MODE FOR CARRYING OUT THE INVENTION

The following Examples illustrate the present invention in further detail. These examples are, however, by no means limitative of the scope of the invention.

In the Examples of this invention, the proportion of a reduced coenzyme Q to the whole coenzyme Q was measured by using a HPLC system incorporated Coulochem (electrochemical detectors; product of ESA Inc.).

PRODUCTION EXAMPLE 1

Production of Reduced Coenzyme $Q_{10}$-1

Oxidized coenzyme $Q_{10}$ (100 g; purity 99.4%) and 60 g of L-ascorbic acid were added to 1,000 g of ethanol, and the reduction reaction was allowed to proceed with stirring at 78° C. After 30 hours, the mixture was cooled to 50° C., and 330 g of ethanol and 70 g of water were added while maintaining the same temperature. This ethanol solution (containing 100 g of reduced coenzyme $Q_{10}$) was cooled to 2° C. at a cooling rate of 10° C./hour with stirring to give a white slurry. The slurry obtained was subjected to filtration under reduced pressure, the wet crystals obtained were washed with cold ethanol, cold water and cold ethanol in that order (the temperature of the cold solvents used for washing being 2° C.) and, further, the wet crystals were dried under reduced pressure (20 to 40° C., 1 to 30 mm Hg) to give 97 g of dry white crystals. All the operations except for drying under reduced pressure were carried out in a nitrogen atmosphere.

PRODUCTION EXAMPLE 2

Production of Reduced Coenzyme $Q_{10}$-2

Oxidized coenzyme $Q_{10}$ (100 g) was dissolved in 1,000 g of heptane at 25° C. An aqueous solution prepared by adding 1,000 ml of water to 100 g of sodium dithionite (purity at least 75%) as a reducing agent was added gradually to the heptane solution with stirring, and the reduction reaction was allowed to proceed at 25° C. and pH 4 to 6. After 2 hours, the aqueous phase was removed from the reaction mixture, and the heptane phase was washed with six 1,000-g portions of a deaerated saturated aqueous solution of sodium chloride. All the above operation were carried out in a nitrogen atmosphere. A 7% (w/w) solution of reduced coenzyme $Q_{10}$ in ethanol (containing 100 g of reduced coenzyme $Q_{10}$) at 50° C. was prepared from the heptane phase by solvent substitution under reduced pressure. Water (50 g) was added to this ethanol solution, and crystallization was carried out by cooling to 2° C. at a rate of 10° C./hour with stirring. All the operations were carried out in a nitrogen atmosphere. The resulting slurry was filtered under reduced pressure, the wet crystals were washed with cold ethanol, cold water and cold ethanol in that order (the temperature of the cold solvents used for washing being 2° C.) and, further, the wet crystals were dried under reduced pressure (20 to 40° C., 1 to 30 mm Hg) to give 97 g of dry white crystals.

EXAMPLE 1

A solution of reduced coenzyme $Q_{10}$ (containing 1% by weight of oxidized coenzyme $Q_{10}$) in soybean oil (reduced coenzyme $Q_{10}$/soybean oil solution=20 mg/ml) was orally administered to male SD strain rats (6 weeks of age) at a dose of reduced coenzyme $Q_{10}$ (containing 1% by weight of oxidized coenzyme $Q_{10}$) of 100 mg/kg and, after 0.5, 1, 2, 3, 4, 5, 6, 8, 12 and 24 hours after administration, blood samples were collected and used for assaying plasma coenzyme $Q_{10}$ (reduced coenzyme $Q_{10}$ and oxidized coenzyme $Q_{10}$) (n=4). Plasma coenzyme $Q_{10}$ was assayed by HPLC. Thus, coenzyme $Q_7$ (0.003 mg), ethanol (1 ml), distilled water (1 ml) and ferric chloride (0.01%) were added to each rat plasma sample (0.2 ml) and, after mixing up, hexane (3 ml) was added thereto and coenzyme $Q_{10}$ was extracted with shaking. After two repetitions of this extraction procedure, the hexane extracts were combined and evaporated to dryness, the residue was again dissolved in 0.25 ml of ethanol, and the solution was injected into the HPLC column. The HPLC conditions were as follows:
column: YMC-Pack (ODS-A303), detection wavelength: 275 nm, mobile phase: methanol (88%)+hexane (12%), flow rate: 1 ml/min (the retention time of reduced coenzyme $Q_{10}$: 25.7 minutes, the retention time of oxidized coenzyme $Q_{10}$: 19.3 minutes).

EXAMPLE 2

Reduced coenzyme $Q_{10}$ (containing 3% by weight of oxidized coenzyme $Q_{10}$) was administered in the same manner as in Example 1, and plasma coenzyme $Q_{10}$ levels were determined.

COMPARATIVE EXAMPLE 1

Oxidized coenzyme $Q_{10}$ was administered in the same manner as in Example 1, and plasma coenzyme $Q_{10}$ levels were determined.

COMPARATIVE EXAMPLE 2

Reduced coenzyme $Q_{10}$ (containing 5% by weight of oxidized coenzyme $Q_{10}$) was administered in the same manner as in Example 1, and plasma coenzyme $Q_{10}$ levels were determined.

The time courses of the plasma coenzyme $Q_{10}$ levels as found in Example 1 and Comparative Example 2 are shown in FIG. 1. It is seen that the sample of Example 1 showed prolonged maintenance of high concentration of coenzyme Q in blood as compared with the plasma coenzyme $Q_{10}$ ($CoQ_{10}$) levels attained following administration of the sample of Comparative Example 2.

TABLE 1

|  | $C_{max}$(µg/ml) | AUC(µg · hr/ml) |
|---|---|---|
| Comparative Example 1 | 1.73(47**) | 12.9(75**) |
| Comparative Example 2 | 3.67(100) | 17.2(100) |

TABLE 1-continued

|  | $C_{max}$(µg/ml) | AUC(µg · hr/ml) |
|---|---|---|
| Example 1 | 4.02(110) | 51.3(298**) |
| Example 2 | 3.97(108) | 47.1(274**) |

**$p < 0.01$ Student t-test shows significant difference against Comparative Example 2

The maximum blood concentrations ($C_{max}$) and the areas under the curve (AUC) as determined based on the assay results obtained in Examples 1 and 2 and Comparative Examples 1 and 2 are summarized in Table 1. It was revealed that, as compared with the composition of Comparative Example 2, the compositions of Example 1 and Example 2 showed no great differences in $C_{max}$ but showed AUC values about three times higher and thus were significantly superior in maintenance of high concentration of coenzyme Q in blood.

The above results indicate that when a composition having a reduced coenzyme Q-to-oxidized coenzyme Q (reduced coenzyme Q:oxidized coenzyme Q) ratio of more than 95:5 is used, not only the plasma coenzyme Q concentration can be increased but also the maintenance of high concentration of coenzyme Q in blood can be prolonged.

EXAMPLE 3

Powder Preparation

Reduced coenzyme $Q_{10}$ (containing 2% by weight of oxidized coenzyme $Q_{10}$) was dissolved in propanol and allowed to be adsorbed on microcrystalline cellulose, followed by drying under reduced pressure. The dried matter was mixed with corn starch under nitrogen to give a powder preparation.

| Reduced coenzyme $Q_{10}$ | 9.8 parts by weight |
|---|---|
| Oxidized coenzyme $Q_{10}$ | 0.2 part by weight |
| Microcrystalline cellulose | 40 parts by weight |
| Corn starch | 55 parts by weight |

EXAMPLE 4

Capsules

According to the formulation given below, a powder preparation was prepared in the same manner as in Example 3 and filled into gelatin capsules in the conventional manner. Capsules filled were sealed, packaged in a nitrogen atmosphere and stored in a refrigerator.

| Reduced coenzyme $Q_{10}$ | 19.6 parts by weight |
|---|---|
| Oxidized coenzyme $Q_{10}$ | 0.4 part by weight |
| Microcrystalline cellulose | 40 parts by weight |
| Corn starch | 20 parts by weight |
| Lactose | 65 parts by weight |
| Magnesium stearate | 3 parts by weight |
| Polyvinylpyrrolidone | 2 parts by weight |

EXAMPLE 5

Soft Capsules

Reduced coenzyme $Q_{10}$ (containing 2% by weight of oxidized coenzyme $Q_{10}$) melted at 50° C. was added to and dissolved in corn oil warmed to the same temperature. Soft capsules were filled with that solution in the conventional manner.

| | |
|---|---|
| Reduced coenzyme $Q_{10}$ | 49 parts by weight |
| Oxidized coenzyme $Q_{10}$ | 1 part by weight |
| Corn oil | 350 parts by weight |

EXAMPLE 6

Tablets

Reduced coenzyme $Q_{10}$ (containing 2% by weight of oxidized coenzyme $Q_{10}$) was dissolved in propanol and allowed to be adsorbed on microcrystalline cellulose, followed by drying under reduced pressure. The dried matter was mixed with corn starch, lactose, carboxymethylcellulose and magnesium stearate in a nitrogen atmosphere and, after addition of an aqueous solution of polyvinylpyrrolidone as a binder, the mixture was granulated in the conventional manner. Talc, as a lubricant, was added to the granules and, after mixing up, the mixture was made into tablets.

The tablets were packaged in a nitrogen atmosphere and stored in a refrigerator.

| | |
|---|---|
| Reduced coenzyme $Q_{10}$ | 19.6 parts by weight |
| Oxidized coenzyme $Q_{10}$ | 0.4 part by weight |
| Corn starch | 25 parts by weight |
| Lactose | 15 parts by weight |
| Carboxymethylcellulose calcium | 10 parts by weight |
| Microcrystalline cellulose | 40 parts by weight |
| Polyvinylpyrrolidone | 5 parts by weight |
| Magnesium stearate | 3 parts by weight |
| Talc | 10 parts by weight |

The invention claimed is:

1. A coenzyme Q composition for maintaining high concentration of coenzyme Q in blood
    which comprises, as the active ingredients, a reduced coenzyme Q represented by the following formula (1), wherein n represents an integer of 1 to 12, and an oxidized coenzyme Q represented by the following formula (2), wherein n represents an integer of 1 to 12, with the proportion of the reduced coenzyme Q to the whole coenzyme Q of more than 95% by weight

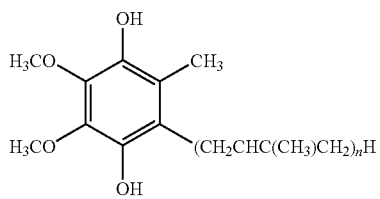

(1)

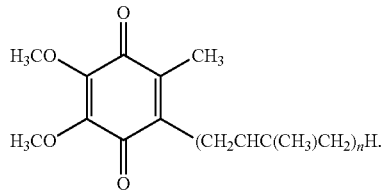

(2)

2. The coenzyme Q composition for maintaining high concentration of coenzyme Q in blood according to claim 1,
    wherein the coenzyme Q is coenzyme $Q_{10}$.

3. coenzyme Q composition for maintaining high concentration of coenzyme Q in blood according to claim 1
    which further comprises an antioxidant substance and/or an antioxidant enzyme.

4. The coenzyme Q composition for maintaining high concentration of coenzyme Q in blood according to claim 3,
    wherein said antioxidant substance is at least one member selected from the group consisting of vitamin E, a vitamin E derivative, vitamin C, a vitamin C derivative, probucol, lycopene, vitamin A, a carotenoid, vitamin B, a vitamin B derivative, a flavonoid, a polyphenol, glutathione, pyrroloquinoline quinone, Pycnogenol, Flavangenol, selenium, a lipoic acid and a lipoic acid derivative.

5. The coenzyme Q composition for maintaining high concentration of coenzyme Q in blood according to claim 3,
    wherein said antioxidant enzyme is at least one member selected from the group consisting of superoxide dismutase, glutathione peroxidase, glutathione-S-transferase, glutathione reductase, catalase and ascorbic acid peroxidase.

6. A method of maintaining the blood coenzyme Q concentration for a prolonged period of time
    which comprises administering a composition comprising a reduced coenzyme Q represented by the following formula (1), wherein n represents an integer of 1 to 12, and an oxidized coenzyme Q represented by the following formula (2), wherein n represents an integer of 1 to 12, with the proportion of the reduced coenzyme Q to the whole coenzyme Q of more than 95% by weight

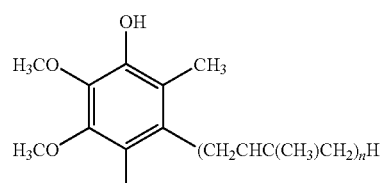

(1)

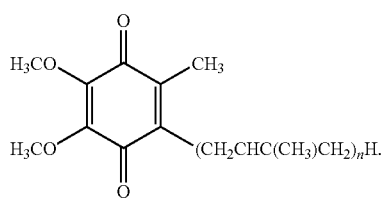

(2)

7. The method according to claim 6,
wherein the dosage form of said composition is an oral formulation.

8. The method according to claim 7,
wherein said oral formulation is in the form of capsules, tablets, a powder or a liquid.

9. The method according to claim 6,
wherein the coenzyme Q is coenzyme $Q_{10}$.

10. The method according to claim 6,
by which the blood coenzyme Q concentration can be maintained at levels not lower than half the maximum blood concentration shown after administration of said composition for at least 8 hours.

11. The coenzyme Q composition for maintaining high concentration of coenzyme Q in blood according to claim 2 which further comprises an antioxidant substance and/or an antioxidant enzyme.

12. The method according to any one of claims 7,
wherein the coenzyme Q is coenzyme $Q_{10}$.

13. The method according to any one of claims 8,
wherein the coenzyme Q is coenzyme $Q_{10}$.

14. The method according to claim 9,
by which the blood coenzyme $Q_{10}$ concentration can be maintained at levels not lower than half the maximum blood concentration shown after administration of said composition for at least 8 hours.

15. The method according to claim 10,
wherein the dosage form of said composition is an oral formulation.

16. The method according to claim 15,
wherein said oral formulation is in the form of capsules, tablets, a powder or a liquid.

\* \* \* \* \*